United States Patent [19]

Baumann

[11] Patent Number: 5,405,980

[45] Date of Patent: Apr. 11, 1995

[54] CONDENSATES AND THEIR USE AS OXYALKYLATION ADJUVANTS

[75] Inventor: Hans-Peter Baumann, Ettingen, Switzerland

[73] Assignee: Sandoz Ltd., Basel, Switzerland

[21] Appl. No.: 21,823

[22] Filed: Feb. 24, 1993

[30] Foreign Application Priority Data

Feb. 26, 1992 [DE] Germany ............... 42 05 844.9

[51] Int. Cl.$^6$ ......................................... C07C 51/367
[52] U.S. Cl. ............................ 554/162; 554/163; 554/170; 554/173; 568/593; 568/602; 564/305; 564/463; 560/8; 560/129
[58] Field of Search ............ 554/162, 163, 170, 173; 568/593, 602; 564/305, 463; 560/8, 129

[56] References Cited

U.S. PATENT DOCUMENTS

| 2,493,486 | 1/1950 | Greenlee | 528/111.5 |
| 4,172,070 | 10/1979 | Scharrer | 260/104 |

FOREIGN PATENT DOCUMENTS

| 93341 | 11/1983 | European Pat. Off. . |
| 98487 | 1/1984 | European Pat. Off. . |
| 270773 | 6/1988 | European Pat. Off. . |
| 370273 | 5/1989 | European Pat. Off. . |
| 335295 | 10/1989 | European Pat. Off. . |
| 335295 | 10/1989 | European Pat. Off. . |
| 353928 | 2/1990 | European Pat. Off. . |
| 1270542 | 6/1968 | Germany . |
| 2628778A1 | 1/1978 | Germany . |
| 3837947A1 | 5/1980 | Germany . |
| 3416289A1 | 11/1985 | Germany . |
| 3534733A1 | 4/1987 | Germany . |
| 3709861A1 | 10/1988 | Germany . |
| 3725080A1 | 2/1989 | Germany . |
| 3923562A1 | 1/1991 | Germany . |
| 1050497 | 12/1966 | United Kingdom . |
| 1556714 | 11/1979 | United Kingdom . |
| 630278 | 9/1978 | U.S.S.R. . |
| 802342 | 2/1981 | U.S.S.R. . |

OTHER PUBLICATIONS

Search Report, Deutsches Patentamt, date 26.Nov.92 (2 sheets) for corresponding FRG application No. P 42 05 844.9.

Search Report, European Patent Office, date 18.May.93 (2 sheets) for corresponding EPO application No. EP 93 81 0114.

Primary Examiner—José G. Dees
Assistant Examiner—Joseph M. Conrad, III
Attorney, Agent, or Firm—Robert S. Honor; Richard E. Vila; Andrew N. Parfomak

[57] ABSTRACT

Condensates (K) of (A) oligohydroxy-$C_{3-8}$-alkanes containing at least 3 hydroxy groups and (B) KOH, that contain at least 5% by weight of $K^+$ and at least one alcoholic hydroxy group are eminently suitable as oxyalkylation catalysts, in particular for the oxyalkylation of ester group-containing substrates, before all of natural, vegetable or animal fats or oils or their modification products.

15 Claims, No Drawings

CONDENSATES AND THEIR USE AS OXYALKYLATION ADJUVANTS

Oxyalkylated, in particular oxyethylated and/or oxypropylated, products are nowadays employed as surfactants in many a field of technique, e.g. in the residual oil recovery, in plastics industry, in cosmetics, in the processing of foods, in the treatment of textile or non-textile substrates, in the production of colours and paints, in the processing of ores or earths, or of back-waters or sludges, and in various recycling processes etc., a group of surfactants particularly worth mention being represented by the oxyalkylated fatty acid esters, especially triglycerides. It is, thus, desired to produce such surfactants in a way as economic as possible and with a yield as high as possible and that with this in the final products the quantity of non-reacted alkylene oxides and/or of undesired by-products (with oxyethylations especially 1,4-dioxane) be as low as possible.

It has now been found that certain KOH/oligohydroxyalkane condensates, as defined below, are surprisingly well suitable as catalysts for oxyalkylations, in particular also for most difficult oxyalkylations of fatty acid esters.

The invention relates to the condensates, their production and their use as adjuvants, in particular as catalysts, for oxyalkylations and also to the oxyalkylation products obtained therewith.

The invention thus provides a process for the production of a condensate (K), wherein (A) at least one oligohydroxyalkane that contains 3 to 8 carbon atoms and at least 3 hydroxy groups is condensed with such an amount of (B) potassium hydroxide that the condensation product (K) contains at least 5% by weight of K+ and at least one alcoholic hydroxy group.

The oligohydroxy compounds (A) contain no more alcoholic hydroxy groups than C-atoms and are, in general, known compounds. As oligohydroxy alkanes (A) come principally into consideration $C_{4-8}$-alkane triols and compounds of the formula

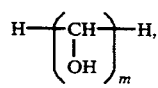

wherein m signifies 3 to 6.

In the oligohydroxyalkanes (A) the alkane chains may be linear or, if they contain 4 or more carbon atoms, also branched or, if they contain 5 or more carbon atoms (in particular 6 carbon atoms), may also be cyclic. There may in particular be mentioned 1,2,4-butanetriol, 1,2,3- or 1,2,6-hexanetriol, 1,2,3-heptanetriol and 1,2,3-octanetriol, and as compounds of formula (I) in particular glycerine, erythritol, arabitol, xylitol, mannitol or sorbitol. Among the mentioned compounds are preferred those with 3 to 6 carbon atoms, in particular those of formula (I), especially glycerine. The oligohydroxyalkanes (A) may be employed as pure substances (e.g. of more than 95% purity) or even in technical quality (e.g. of 85 to 95% purity).

The potassium hydroxide (B) may be employed as a pure substance or also in the form of technical potassium hydroxyde, e.g. as KOH of 80 to 100% purity, a technical KOH of 85 to 90% purity being well suitable for the process of the invention.

The relative quantities of (A) and (B) are suitably chosen so that at least 5% by weight of K+ are present in the final product and the final product contains at least one hydroxy-group on average per molecule of product. Advantageously there are employed 2 to 26 vals of (A) per each mole of (B) [1 val of (A)=1 mole of (A) divided by the number of alcoholic hydroxy groups in the molecule]. With particular advantage there are employed 1 to 8 moles of (A) per each mole of (B); advantageously 6 to 20 vals, in particular 2 to 8 moles, preferably 3 to 7.5 moles of (A) per each mole of (B).

The condensation of (A) in the presence of (B) takes place suitably under an inert atmosphere, preferably under a nitrogen blanket and with elimination of reaction water at elevated temperature, advantageously at temperatures $\geq 60°$ C. Although it is also possible to condense at temperatures up to 160° C., e.g. between 100° and 120° C., it is preferred to carry out the condensation at temperatures in the range of 60° to 100° C. preferably 75° to 98° C. and to eliminate the reaction water under reduced pressure The condensation is advantageously continued until the formation of reaction water diminishes and all of the potassium of the employed potassium hydroxide has replaced the hydrogen of alcoholic hydroxy groups, and preferably a part of the remaining hydroxy groups have condensed to ether groups, so that in the reaction product there are also present oligocondensates of (A) as potassium salts. Advantageously the condensation is continued until 2 to 200, preferably 5 to 50 mole % of condensation water in excess over that resulting from the plain potassium alcoholate formation is eliminated. Preferably the condensation water is removed after diminishing of its formation (preferably under reduced pressure). The whole condensation, including the elimination of water, is advantageously carried out within 2 to 10, preferably 2½ to 6 hours, in which the condensation reaction may e.g. last 1½ to 3 hours and the remaining time is determined essentially by the employed apparatus and the regulation of the vacuum for the elimination of the water of condensation. Depending on the employed compound (A) and the weight ratio (A)/(B) the suitable condensation temperatures and durations may vary and may be optimized by means of a few preliminary tests. The relative quantities of (A) and (B) are advantageously chosen so that in the obtained condensate (K) the K+-content is in the range of 5 to 22, preferably 5.4 to 22, more preferably 7 to 15% by weight.

The so produced condensates (K) are in general liquid to thick or even pasty to solid and are practically odourless. They are readily soluble in water and also readily soluble in or miscible with vegetable oils. The liquid to thick products are preferred. Their rotational viscosity at 60° C. is preferably in the range of 300 to 2000 mPa.s.

The condensates (K) obtainable by the above process serve as adjuvants, in particular as catalysts, for oxyalkylations in particular with (C) at least one cyclic D-oxide wherein D signifies ethylene, propylene, butylene or styrene.

As oxyalkylations come here into consideration those of compounds containing active hydrogens (principally of alcohols, amines, carboxylic acids or carboxylic acid amides) as well as those of compounds that contain no such active hydrogen atoms (in particular of saturated and/or unsaturated fatty acid esters). Of particular relevance are the oxalkylations of (F) natural, optionally modified, ester group-containing oils, fats, waxes and/or resins.

As modified oils, fats, waxes or resins come mainly into consideration ester group-containing modifications (e.g. their partial saponification, hydrogenation, oxidation, alcoholysis and/or transesterification products and/or oligomerization products of unsaturated fatty acid esters). Of particular relevance is the oxyalkylation of fatty acid triglycerides as they occur as natural oils or fats, be it in the form of technical triglycerides mixtures or as refined triglycerides, in which the ester-forming fatty acids contain e.g. 6 to 24 carbon atoms and may be saturated, unsaturated and/or hydroxy group-containing, or further of their alcoholysis resp. transesterification products to fatty acid esters of lower alkanols (e.g. methyl esters or ethyl esters) or of natural esters of higher alcohols. The following may in particular be mentioned: vegetable and animal oils or fats (e.g. cottonseed oil, peanut oils, linseed oil, corn oil, olive oils, rapeseed oils, safflor oil, sesame oil, soybean oil, sunflower oil, palm-kernel oil, palm oil, coconut oil, cocoa butter, shea fat, butter fat, beef tallow, mutton tallow, lard-fat, anchovy oil, whale oil, seal oil, mackerel oil, herrings oil, capelin oil, jojoba oil, castor oil and babassu oil), hydrogenated oils, metiloil, vegetable or animal recent waxes (carnauba wax, japanese wax, candelilla wax, rice germ oil wax, ouricoury wax, bees wax, shellack wax, lanoline) and fossile vegetable waxes (e.g. montan wax), ester group-containing mineral waxes (ceresin, ozokerite) and ester group-containing oxidized hydrocarbon waxes or further partially saponified triglycerides. Of particular relevance among them are the natural vegetable oils, before all those in which at least 35 mol %, preferably at least 50 mol %, of the ester-forming fatty acids are unsaturated acids (principally myristoleic, palmitoleic, oleic, gadoleic, erucic, linoleic and/or linolenic acid), the tallow fats (principally beef tallow, mutton tallow, lard-fat and mixed tallow fats) and the methyl esters of the respective fatty acid mixtures (e.g. metiloil).

Further there may e.g. also be employed sorbitan mono-, di- or triesters of higher fatty acids, e.g. sorbitan mono-, di- or trilaurate, -palmirate, -oleate or -stearate.

For oxyalkylation there may be employed as (C) conventional alkylene oxides (in particular oxiranes), e.g. ethylene oxide, propylene oxide, butylene oxide and/or styrene oxide. Since oxyalkylation, in particular of (F), serves mainly for incrementing the hydrophilicity of the products, ethylene oxide is principally employed for the purpose and, in addition to ethylene oxide, optionally propylene oxide, butylene oxide and/or styrene oxide. Advantageously at least one half (i.e. at least 50 mol %) of the employed oxiranes (C) is ethylene oxide; with particular advantage at least 80 mol % thereof is ethylene oxide. Preferably at least 10 moles, advantageously 10 to 200 mols, in particular 20 to 150 mols, of ethylene oxide are added per mol of substrate, in particular of (F); other oxides (C), if they are also employed, are preferably employed in such amounts that correspond to 1 to 20 mol %, preferably 1 to 10 mol %, of the employed amount of ethylene oxide.

The use of condensation products (K) in which (A) is glycerine is to be particularly emphasized, before all in the oxyalkylation of triglycerides.

The oxyalkylation may be carried out analogously to conventional oxyalkylations, in general under an inert atmosphere (e.g. with displacement of air oxygen by gaseous nitrogen) under normal, reduced or even increased pressure and at temperatures that are advantageously in the range of 110° to 200° C., preferably $\leq 180°$ C., in particular in the range of 140° to 180° C. Most oils may be excellently oxyalkylated according to the invention at temperatures in the range between 150° to 180° C., in particular at 160° to 175° C.

The oxyalkylation adjuvant (K) of the invention is suitably employed in such amounts that are efficient to bring about oxyalkylation. The adjuvant (K) of the invention is advantageously employed in such amounts that correspond to at least 2 g, preferably 2 to 25 g, in particular 3 to 15 g $K^+$ per mol of substrate. The suitable and in particular optimum amount of (K) may vary, depending on the substrate and the alkylene oxide and may be determined, respectively optimized, by means of a few preliminary tests.

As an orientative test method there may be set e.g. as a standard that a certain kind and amount of catalyst (K) is readily suitable for the oxyalkylation of a certain substrate, in particular (F), if at 170° C. and normal pressure, after displacement of the air oxygen with gaseous nitrogen and feeding-in of ethylene oxide, the oxyethylation has started within 3 hours.

The substrate, in particular (F), and the catalysts (K) are suitably chosen so that at least at the oxyalkylation temperature the mixture is liquid and (K) is dissolved in the substrate to be oxyalkylated, in particular in (F).

By means of the process of the invention and using the catalyst (K) of the invention oxyalkylations, even of substrates that are otherwise very difficult to oxyalkylate, in particular of oils or fats that are free of active hydrogens, may be carried out surprisingly easily and well, the yield of oxyalkylated product being very high and the obtained products being substantially free of undesired by-products. By the oxyalkylation of fatty acid esters (F) according to the invention there are obtainable oxyalkylated products whose hydroxyl number may vary depending on the substrate and on the conditions, and is in general relatively high (it is mainly in the range of 30 to 300) but is in particular lower than the hydroxyl number obtainable comparatively by the corresponding oxyalkylation of the same amount as (F) of the fatty alcohols corresponding to the fatty acid radicals in the esters (F), in particular in the range of 2 to 98, preferably 10 to 95, more preferably 50 to 95% thereof.

The highly efficient catalysts (K) of the invention are obtainable in an astonishingly simple way and in optimal yield as here described and are distinguished by their efficiency and storage stability.

In the following Examples the percentages are by weight; the temperatures are indicated in degrees Celsius. The oxyethylation products produced in Example A to T do not impair the ecological ambient and are biodegradable. They are of surface-active character and are suitable as emulsifiers and as levelling agents for disperse dyes.

EXAMPLE 1

In a 5-necked sulphonation flask 460.5 g of glycerine are heated with 62.3 g of technical 90% KOH under $N_2$ to 90° C. inner temperature, with good stirring. The mixture is stirred for two hours at this temperature, the reaction water is then distilled off at 135 mbar, then the vacuum is gradually increased (after 30 minutes to 100 mbar and after 60 minutes to 35 mbar) and distillation is continued at 30–35 mbar until no further water passes over (about 1 to 2 hours). The heating is then turned off, the mixture is allowed to cool and is discharged. There are obtained 494.2 g of catalyst ($K_1$); there are collected 23.6 g of clear reaction water as distillate, a small portion (about 3 g) being dragged along by the vacuum.

The product ($K_1$) contains 7.9% $K^+$.

Viscosity at 60° C.=750 mPa.s.

The following table contains further examples of catalysts ($K_2$) to ($K_9$) of the invention, which are produced analogously as described in Example 1 and which are characterized by component (A) and the $K^+$-content.

EXAMPLES 2 TO 9

Catalysts ($K_2$) to ($K_9$)

| (K) | (A) | % $K^+$ |
| --- | --- | --- |
| ($K_2$) | glycerine | 13.96 |
| ($K_3$) | glycerine | 21.56 |
| ($K_4$) | glycerine | 16.2 |
| ($K_5$) | glycerine | 8.86 |
| ($K_6$) | glycerine | 9.0 |
| ($K_7$) | butanetriol-1,2,4 | 8.5 |
| ($K_8$) | 1,2,6-hexantriol | 5.49 |
| ($K_9$) | D-sorbitol | 8.84 |

OXYALKYLATION EXAMPLES

EXAMPLE A 110.0 g of technical rapeseed oil (average molecular weight MW=880) and 5.5 g of catalyst ($K_6$) are given into a 5-necked sulphonation flask of 500 ml capacity and heated with stirring to 115°-125° C., then evacuation is carried out in three successive steps, each with water-jet vacuum (about 40 mbar) and the vacuum is released with nitrogen; then evacuation is carried out a fourth time and the vacuum is then released with ethylene oxide. 275.0 g of ethylene oxide are additioned within four hours at 160°-170° C.

There are obtained 390.5 g of oxyethylation product (addition product of 50 mols of ethylene oxide to 1 mol of rapeseed oil in the presence of the employed catalyst).

EXAMPLE B

The procedure is carried out as described in Example A, with the difference that instead of 5.5 g of catalyst ($K_6$) there are employed 3.3 g of catalyst ($K_2$) and 30 mols of ethylene oxide are additioned per mol of rapeseed oil.

EXAMPLE C

The procedure is carried out as described in Example A, with the difference that instead of 5.5 g of catalyst ($K_6$) there are employed 1.9 g of catalyst ($K_6$) and 120 mols of ethylene oxide are additioned per mol of rapeseed oil.

EXAMPLE D

The procedure is carried out as described in Example A, with the difference that instead of 5.5 g of the catalyst ($K_6$) there are employed 11 g of catalyst ($K_7$) and 10.1 mols of ethylene oxide are additioned per mol of rapeseed oil.

EXAMPLE E

The procedure is carried out as described in Example D, with the difference that instead of 11 g of catalyst ($K_7$) there are employed 11 g of catalyst ($K_8$) and 20 mols of ethylene oxide are additioned per mol of rapeseed oil.

EXAMPLE F

The procedure is carried out as described in Example A, with the difference that instead of rapeseed oil there is employed soybean oil and per mol of soybean oil there are additioned 40 mols of ethylene oxide.

EXAMPLE G

The procedure is carried out as described in Example F, with the difference that per mol of soybean oil there are additioned 20 mols of ethylene oxide.

EXAMPLE H

The procedure is carried out as described in Example A, with the difference that per mol of rapeseed oil there are additioned 70 mols of ethylene oxide.

EXAMPLE I

The procedure is carried out as described in Example A, with the difference that instead of 5.5 g of catalyst ($K_6$) there are employed 2.75 g of catalyst ($K_3$) and per mol of rapeseed oil there are additioned 20 mols of ethylene oxide.

EXAMPLE J

The procedure is carried out as described in Example A, with the difference that instead of 5.5 g of catalyst ($K_6$) there are employed 11 g of catalyst ($K_1$) and 24 mols of ethylene oxide are additioned per mol of rapeseed oil.

EXAMPLE K

The procedure is carried out as described in Example A, with the difference that instead of rapeseed oil there is employed the same quantity of metiloil and instead of the 5.5 g of catalyst ($K_6$) there are employed 22 g of catalyst ($K_5$) and 35 mols of ethylene oxide are additioned per mol of metiloil.

EXAMPLE L

The procedure is carried out as described in Example K, with the difference that instead of 22 g of catalyst ($K_5$) there are employed 16.5 g thereof and 4.2 mols of ethylene oxide are additioned per mol of metiloil.

(Metiloil is a commercial technical fatty acid methylester mixture with saponification number 170-200, acid number 1-12 and average molecular weight MW=298).

EXAMPLE M

The procedure is carried out as described in Example A, with the difference that instead of 5.5 g of catalyst ($K_6$) there are employed 11 g of catalyst ($K_9$) and 40 mols of ethylene oxide are additioned per mol of rapeseed oil.

EXAMPLE N

The procedure is carried out as described in Example A, with the difference that instead of rapeseed oil there is employed soybean oil and instead of 5.5 g of catalyst ($K_6$) there are employed 11 g of catalyst ($K_9$) and per mol of soybean oil there are additioned 50 mols of ethylene oxide.

EXAMPLE O

The procedure is carried out as described in Example N, with the difference that instead of soybean oil there is employed sunflower oil and 35 mols of ethylene oxide are additioned per mol of sunflower oil.

EXAMPLE P

The procedure is carried out as described in Example O, with the difference that instead of 11 g of catalyst ($K_9$) there are employed 11 g of catalyst ($K_6$) and per mol of sunflower oil there are additioned 50 mols of ethylene oxide.

EXAMPLE Q

The procedure is carried out as described in Example A, with the difference that instead of rapeseed oil there is employed jojoba oil and instead of 5.5 g of catalyst ($K_6$) there are employed 11 g of catalyst ($K_6$) and per mol of jojoba oil there are additioned 30 mols of ethylene oxide.

EXAMPLE R

The procedure is carried out as described in Example Q, with the difference that instead of jojoba oil there is employed the same amount of lard-fat.

EXAMPLE S

The procedure is carried out as described in Example Q, with the difference that instead of jojoba oil there is employed the same amount of castor oil.

EXAMPLE T

The procedure is carried out as described in Example N, with the difference that instead of soybean oil there is employed sorbitan trioleate and 12 mols of ethylene oxide are additioned per mol of sorbitan trioleate.

I claim:

1. An oxyalkylation process which comprises the process step of:
   oxyalkylating a compound in the presence of a condensate (K) which is the condensate of:
   (A) at least one oligohydroxyalkane containing 3 to 8 carbon atoms and containing at least 3 hydroxy groups, with,
   (B) potassium hydroxide,
   wherein the condensate (K) contains at least 5% by weight of $K^+$ and at least one alcoholic hydroxy group.

2. A process according to claim 1 wherein the compound is:
   (F) a natural, optionally modified ester-containing group containing oil, fat, wax, and/or resin.

3. A process according to claim 2, wherein one or more (F) natural, optionally modified ester-group containing oils, fats, waxes and/or resins is reacted with (C) at least one cyclic D-oxide selected from the group consisting of ethylene oxide, propylene oxide, butylene oxide and styrene oxide.

4. A process according to claim 2, wherein (K) is used in such an amount that corresponds to 2 to 25 g of $K^+$ per mol of (F).

5. A process according to claim 2 wherein (F) is soya oil.

6. A process according to claim 2 wherein (F) is tallow.

7. A process according to claim 2 wherein (F) is olive oil.

8. A process according to claim 2 wherein (F) is peanut oil.

9. A process according to claim 2 wherein (F) is a fatty acid triglyceride.

10. A process according to claim 1, wherein:
    (C) at least one cyclic D-oxide is used to oxzalkzlate the compound in the presence of the condensate (K) where D-oxide is selected from the group consisting of: ethylene oxide, propylene oxide, butylene oxide and styrene oxide.

11. A process according to claim 1, wherein (C) is ethylene oxide and optionally at least one further cyclic D-oxide which is selected from the group consisting of: propylene oxide, butylene oxide and styrene oxide.

12. A process according to claim 1, wherein the oxyalkylation is carried out at temperatures less than or equal to 180° C.

13. A process according to claim 12, wherein the oxyalkylation is carried out at temperatures in the range of 150° to 180° C.

14. A process according to claim 1, wherein (A) is a $C_{4-8}$-alkanetriol or is a compound of formula

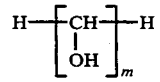

wherein m signifies 3 to 6, or a mixture of such compounds.

15. A process according to claim 14 wherein (A) is glycerine.

* * * * *